United States Patent
Karpas et al.

(10) Patent No.: US 8,942,926 B2
(45) Date of Patent: *Jan. 27, 2015

(54) METHOD FOR THE DIAGNOSIS OF PATHOLOGICAL CONDITIONS IN ANIMALS

(75) Inventors: Zeev Karpas, Omer (IL); Shmuel Marcus, Kfar-Saba (IL); Moshe Golan, Arad (IL)

(73) Assignee: Q-Scent Ltd. (IL)

( * ) Notice: Subject to any disclaimer, the term of this patent is extended or adjusted under 35 U.S.C. 154(b) by 1155 days.

This patent is subject to a terminal disclaimer.

(21) Appl. No.: 12/456,591

(22) Filed: Jun. 18, 2009

(65) Prior Publication Data

US 2009/0325191 A1 Dec. 31, 2009

Related U.S. Application Data

(63) Continuation-in-part of application No. 11/007,365, filed on Dec. 8, 2004, now Pat. No. 7,933,719, which is a continuation of application No. 10/079,624, filed on Feb. 20, 2002, now abandoned, which is a continuation-in-part of application No. 09/813,523, filed on Mar. 21, 2001, now Pat. No. 7,056,745, and a continuation-in-part of application No. PCT/IL02/00087, filed on Jan. 31, 2002.

(30) Foreign Application Priority Data

| Feb. 1, 2001 | (IL) | 141233 |
| Nov. 22, 2001 | (IL) | 146698 |

(51) Int. Cl.
| G01N 33/48 | (2006.01) |
| C12Q 1/04 | (2006.01) |
| A61B 10/00 | (2006.01) |

(52) U.S. Cl.
CPC ........... *C12Q 1/04* (2013.01); *A61B 2010/0074* (2013.01)
USPC .................... 702/19; 435/29; 702/22; 703/12

(58) Field of Classification Search
None
See application file for complete search history.

(56) References Cited

U.S. PATENT DOCUMENTS

| 4,001,213 A | 1/1977 | Hershman et al. |
| 4,080,488 A | 3/1978 | Chen et al. |
| 5,109,691 A | 5/1992 | Corrigan et al. |
| 5,447,556 A | 9/1995 | Pleil et al. |
| 5,856,616 A | 1/1999 | Maswadeh et al. |
| 6,387,329 B1 | 5/2002 | Lewis et al. |
| 6,428,748 B1 | 8/2002 | Wallach |

FOREIGN PATENT DOCUMENTS

| WO | 00/20852 A1 | 4/2000 |
| WO | 02/061425 A2 | 8/2002 |

OTHER PUBLICATIONS

Lawrence, P.J. et al. "Spectrophotometric quantitation of vaginal fluid trimethylamine and comparative performance of olfactory trimethylamine (KOH whiff test) detection and a new colorimetric chemical test," Clinical Chemistry, vol. 45 No. 6 Part 2, Jun. 1999, p. A162 XP001118327 51st Annual Meeting of the American Association of Clinical Chemistry, New Orleans, LA, USA, Jul. 25-29, 1999 IISN: 0009-9147 abstract.
Suh, Ja Won, et al. "Urinary Polymine Evaluation for Effective Diagnonosis of Various Cancers" J. Chromatog B, V of 688 (1997) pp. 179-186.
Chen, K.C.S., et al. "Biochemical Diagnosis of Vaginitis: Determination of Diarrines in Vaginal Fluid" J. Infect. Dis vol. 145 (1982) pp. 337-345.
Karpas, Z, "Ion Mobility Spectromerty of Aliphatic and Aromatic Amines," Anal. Chem, vol. 61, (1989), pp. 684-689.
Baumbach, J. I., et al, Ion Mobility Spectrometry: Arriving on Site and Moving Beyond a Low Profile, Appl. Spectrose, vol. 53, (1999), pp. 338A-355 A.
Karpas et al., "The Structure of Protonated Diaminesand Polymaines," Struct. Chem., vol. 5, (1994) pp. 135-140.
Baumbach, J. I., et al, Appl. Spectrose, Ion Mobility Spectrometry: Arriving on Site Anad Moving Beyond a Low Profile, vol. 53, (1999), pp. 338A-355 A.
Karpas, Z, "Ion Mobility Spectromerty of Aliohatic and Aromatic Amines" Chem, Vo. 61, (1989), pp. 684-689.
Chen et al. "Amine Content of Vaginal Fluid from Treated and Untreated Patients with Nonspecific Vaginitis" J. Clin. Invest. (1979) pp. 828-835.
International Search Report, PCT/IL2010/000483, dated Nov. 5, 2010.
Chaim Walter et al: "New technology for diagnosis of bacterial vaginosis," European Journal of Obstetrics, Gynecology, and Reproductive Biology Nov. 10, 2003 LNKD-PUBMED:14557018, vol. 111, No. 1, Nov. 10, 2003, pp. 83-87, XP002605532.
Karpas Z et al: "Novel application for ion mobility spectrometry: Diagnosing vaginal infections through measurement of biogenic amines" Analytica Chimlca Acta 20021209 NL LNKDD01: 10.1016/S0003-267(02)01007-3, vol. 474, No. 1-2, Dec. 9, 2002, pp. 115-123, XP002605533.

*Primary Examiner* — Eric S Dejong
(74) *Attorney, Agent, or Firm* — Lerner, David, Littenberg, Krumholz & Mentlik, LLP

(57) ABSTRACT

A method for diagnosing a disease or pathological condition in a non-human animal. An ion mobility spectrometry measurement (IMS) or a differential mobility spectrometry (DMS) is carried out on a body sample from the animal to determine an amount of ions formed by at least two biogenic amines contained in the sample. A ratio is calculated of the amounts of ions formed by the different biogenic amines in the sample, wherein the ratio is indicative of the presence or absence of the disease or pathological condition.

14 Claims, 21 Drawing Sheets

METHOD FOR THE DIAGNOSIS OF PATHOLOGICAL CONDITIONS IN ANIMALS

CROSS-REFERENCE TO RELATED APPLICATIONS

This application is a continuation-in-part of U.S. application Ser. No. 11/007,365, now U.S. Pat. No. 7,933,719, filed on Dec. 8, 2004, which is a continuation of U.S. application Ser. No. 10/079,624, filed on Feb. 20, 2002 (abandoned), which is a continuation-in-part of U.S. application Ser. No. 09/813,523, filed on Mar. 21, 2001, the disclosures of which are incorporated herein by reference.

FIELD OF THE INVENTION

The invention relates to methods for diagnosing pathological conditions in non-human animals.

BACKGROUND OF THE INVENTION

Levels of biogenic amines in human body fluids have been used to diagnose pathological conditions. For example, elevated levels of certain biogenic amines in urine have been shown to indicate the presence or the likelihood of the presence of a cancer (see, for instance, Suh, J W, Lee, S H, Chung, B C, Park, J, *Urinary Polyamine Evaluation for Effective Diagnosis of Various Cancers*, Journal of Chromatography B, 1997, Vol. 688, Iss 2, pp. 179-186). Similarly, it has been shown that elevated levels of biogenic amines in vaginal discharge and fluids suggests the presence of different types of vaginal diseases. (see, for instance, C. S. Chen, R. Amsel, D. A. Eschenbach and K. K. Holmes, *Biochemical Diagnosis of Vaginitis: Determination of Diamines in Vaginal Fluid*, J. Infectious Disease 145 (1982), pp. 337-345).

Body fluids may include e.g. urine, blood, serum, saliva, vaginal discharge and fluids, etc. Further, samples in which the presence of biogenic amines may be determined may not be fluids, but, e.g., skin and tissues, sweat samples, etc. Even direct sniffing of skin or breath exhaled by a subject may provide information in this respect. This should be understood whenever body fluids are mentioned in this application.

Biochemical reactions and degradation processes of dead cells are accompanied by the breakdown of peptides and DNA leading to the formation of amines. One of the processes of particular interest is the breakdown of amino acids and the production of diamines and polyamines. For example, decarboxylation of histidine, ornithine, lysine, produces histamine, putrescine and cadaverine, respectively.

Ion Mobility Spectrometry (also, briefly, IMS) is an analytical method that has been applied to the determination of aliphatic and aromatic amines. See, for instance, Z. Karpas, *Ion Mobility Spectrometry of Aliphatic and Aromatic Amines*, Anal. Chem. 61 (1989), 684. An apparatus for carrying out this method—the Ion Mobility Spectrometer (IMS)—is used primarily for detection, identification and monitoring of trace amounts of gases and vapors. It is particularly suitable for detection of compounds that have high proton affinity and form stable positive ions, or for compounds that have a high electronegativity and readily form stable negative ions. IMS is discussed in J. I. Baumbach and G. A. Eiceman, Appl. Spectrosc. 1999, vol. 53, pp. 338A 355A.

BRIEF SUMMARY OF THE INVENTION

In accordance with the present invention, Applicants have discovered a method for diagnosing a disease or pathological condition in a non-human animal comprising: obtaining a body sample from the animal; carrying out an ion mobility spectrometry (IMS) or a differential mobility spectrometry (DMS) measurement on the sample thereby determining an amount of ions formed by at least two biogenic amines contained in the sample; and calculating a ratio of the amounts of ions formed by the different biogenic amines in the sample, wherein the ratio is indicative of the disease or pathological condition.

In accordance with the present invention, the body sample is taken from the group consisting of male genitalia, female genitalia, udder, liver, heart, muscle, brain, tongue, throat, lungs, skin, and lymph node.

In accordance with another embodiment of the present invention, the disease or pathological condition is selected from the group consisting of bacterial vaginosis, inflammation, cancer, and bronchitis.

In accordance with another embodiment of the present invention, the disease or pathological condition is caused by bacteria, viruses, anaerobic microorganisms, and fungi.

In accordance with another embodiment of the present invention, the body sample is a sample of vaginal fluid, wherein at least one of the amines present in the sample is trimethylamine, and wherein the pathological conditions comprise vaginal disorders.

In accordance with another embodiment of the present invention, the invention further comprises calculating a ratio of the amounts of ions formed by trimethylamine and ions formed by all biogenic amines present in the sample, and diagnosing the presence of bacterial vaginosis if the ratio is above a predetermined threshold.

In accordance with another embodiment of the present invention, the predetermined threshold is 0.4

In accordance with another embodiment of the present invention, the invention comprises diagnosing the presence of bacterial vaginosis if a ratio TMA signal is above a predetermined threshold.

In accordance with another embodiment of the present invention, the invention comprises calculating a ratio of the amounts of ions formed by trimethylamine and ions formed by all biogenic amines present in the sample, and diagnosing an absence of bacterial vaginosis if the ratio is below a predetermined threshold.

In accordance with another embodiment of the present invention, the predetermined threshold is 0.2

In accordance with another embodiment of the present invention, the invention comprises calculating a ratio of the amounts of ions formed by trimethylamine and ions formed by all biogenic amines present in the sample, and diagnosing an absence of bacterial vaginosis if a TMA signal is below a predetermined threshold.

In accordance with another embodiment of the present invention, abnormally high amounts of putrescine or cadaverine indicate a pathological condition.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 14 is a graphical representation showing the mobility spectra such as those of FIG. 13, but obtained by adding KOH to the mixture;

FIG. 15 is a graphical representation showing the mobility spectra such as those of FIGS. 13 and 14, but obtained after adding firstly nitric acid and then KOH;

FIG. 16 is a graphical representation showing the mobility spectra, similar to those of FIGS. 13, 14 and 15, but of a sample of vaginal fluid with a cotton Q-tip;

FIG. 17 is a graphical representation showing the mobility spectra, similar to those of FIGS. 13, 14 and 15, but of another sample of vaginal fluid with a cotton Q-tip;

FIG. 18 is a graphical representation showing the mobility spectra, similar to those of FIGS. 13, 14 and 15, but of another sample of vaginal fluid with a cotton Q-tip;

FIG. 19 is a graphical representation showing the mobility spectra, similar to those of FIGS. 13, 14 and 15, but of a sample of a piece of chicken collected after one day in a refrigerator;

FIG. 20 is a graphical representation showing the mobility spectra, similar to those of FIGS. 13, 14 and 15, but of another sample of a piece of chicken collected after one day in a refrigerator.

FIG. 21 is a graphical representation showing the mobility spectra, similar to those of FIGS. 13, 14 and 15, but of another sample of a piece of chicken collected after one day in a refrigerator.

DETAILED DESCRIPTION

Figure 1:
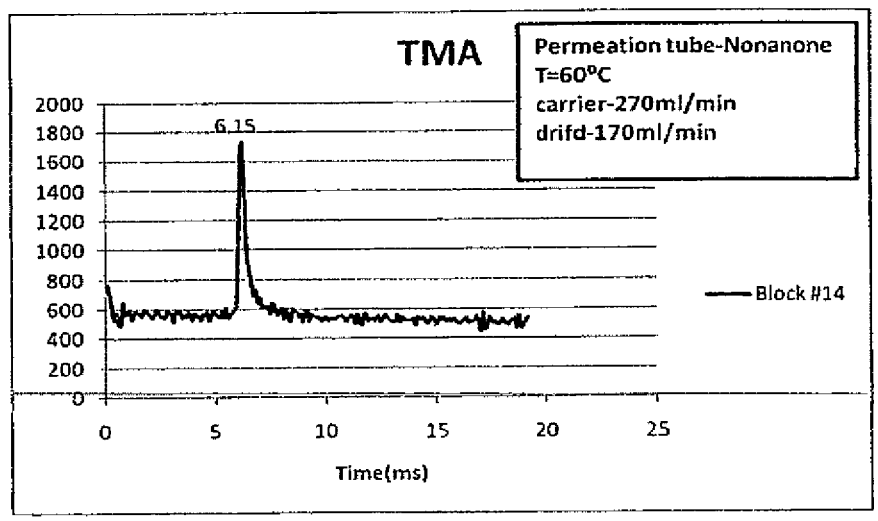
FIG. 1 shows the mobility spectrum obtained with trimethylamine ("TMA") for calibration.

The present invention is based on the finding that detection of biogenic amines can be used for the diagnosis of pathological conditions, such as bacterial vaginosis, in non-human animals. Accordingly, the present invention provides a method for diagnosing pathological disorders in non-human animals. The pathological disorder may be, for example, a vaginal disorder such as bacterial vaginosis.

In accordance with the invention, a body sample is obtained form a non-human animal and is analyzed to determine levels of one or more biogenic amines. A body fluid sample, such as saliva, vaginal discharge, etc., may be collected for example using a swab. Samples of other body fluids, such as blood, urine, semen, etc. can be collected in a vial or other vessel and analyzed. Samples that consist of tissues like feathers, hair, nails or soft body tissues can be removed from the animal and measured after proper pretreatment.

The biogenic amine or amines to be determined may be any one or more of diamines and polyamines and their derivatives, such as acetylamines, trimethylamine ("TMA"), diamines like putrescine and cadaverine as well as polyamines like spermidine and spermine.

One preferred embodiment of the invention comprises the following steps:

(1) A sample is obtained from a non-human animal subject, as explained above. The biogenic amines in the sample, including, but not limited to, a urine sample, may be pre-concentrated, for example, by contacting the sample with a solid support such as a fiber, with a suitable coating for selective absorption of the amines. Desorption of the pre-concentrated amines in vapor form may be carried out by heating (thermal desorption) or by applying chemicals that release the amines from the support.

(2) Amines are emitted from the sample due to their natural volatility. Enhancement of vapor emanation may be carried out by the addition of an appropriate chemical reagent, such as an alkaline solution (e.g. KOH, NaOH, and/or ammonia), that transforms complex amine compounds, like salts and acidic forms, to more volatile forms.

(3) Vapors emanating from the sample are ionized usually by attachment of one or several protons from a reagent gas that forms reactant ions.

(4) The level of one or more ions in the vapor is determined by introducing the vapor into a device for the detection of amines in the sample. The device may be, for example, an ion mobility spectrometer ("IMS") or differential mobility spectrometer ("DMS") which separates the ions according to their mobility or mass by application of an electric field. Other devices for the detection of gas phase ions may also be used in the invention.

The signal intensities in an IMS derived from biogenic amines without an alkali solution are negligibly small. Addition of an alkali solution leads to enhanced emanation of volatile amines, such as trimethylamine, while less volatile amines are hardly seen in the mobility spectrum. Immersion in hot water (94° C.) results in boiling off the volatile compounds, while the less volatile ones are still barely observed. However, pretreatment with acid, followed by the alkaline solution, leads to emanation of volatile amines at room temperature, and of the less volatile amines when the example is immersed in hot water.

The overall effect of the process of the invention is an enhancement of emanation of all amines by addition of an alkaline solution (a fact well known), but also a selective enhancement of emanation of less volatile amines by combining acid pretreatment with heat. Thus, the presence of putrescine and cadaverine can only readily be noticed once both pretreatment with acidification and heat are applied to the sample.

(6) The level of one or more amines in the sample is determined from the levels of ions derived from amines as determined in the previous step.

(7) The presence of certain biogenic amines and the ratio between them is used for diagnosing a pathological condition of the animal from which the sample was collected.

In one embodiment of the invention, the pathological condition to be diagnosed is bacterial vaginosis. In this embodiment, the level of TMA ions in a sample of vaginal fluid of a non-human animal is determined. In a preferred embodiment, the total amount of amine ions in the sample is measured, and if the number of TMA ions is above a predetermined threshold, such as 40% of the total number of amine ions (or a signal intensity that is above a predetermined threshold), the presence of bacterial vaginosis in the animal is recognized, while if the number of TMA ions is below the threshold, the absence of bacterial vaginosis is recognized.

In another embodiment, levels of putrescine and cadaverine are measured, and if the number of their ions is above a predetermined threshold of the total number of amine ions, various pathological conditions are suspected.

The invention thus provides a method for diagnosing a disease or pathological condition in a non-human animal comprising:

obtaining a body sample from the animal;

carrying out an ion mobility spectrometry measurement or a differential mobility spectrometry on the sample, thereby determining an amount of ions formed by at least two biogenic amines contained in the sample; and calculating a ratio of the amounts of ions formed by the different biogenic amines in the sample, wherein the ratio is indicative of the disease or pathological condition.

The body sample may be taken, for example, from male genitalia, female genitalia, udder, liver, heart, muscle, brain, tongue, throat, lungs, skin, and lymph node. The disease or pathological condition may be selected, for example, from bacterial vaginosis, inflammation, cancer, and bronchitis. The disease or pathological condition may be caused, for example, by bacteria, viruses, anaerobic microorganisms, or fungi.

The body sample may be, for example, a sample of vaginal fluid, wherein at least one of the amines comprises trimethylamine, and wherein the pathological conditions comprise vaginal disorders. The amines may comprise putrescine or cadaverine. In another embodiment, abnormally high amounts of putrescine or cadaverine indicate a pathological condition.

In one embodiment of the invention, the method comprises calculating a ratio of the amounts of ions formed by trimethylamine and ions formed by all biogenic amines present in the sample, and diagnosing the presence of bacterial vaginosis if the ratio is above a predetermined threshold. The predetermined threshold may be, for example, 0.4. Alternatively, the method may comprise diagnosing the presence of bacterial vaginosis if the TMA signal is above a predetermined threshold.

In another embodiment, the method comprises calculating a ratio of the amounts of ions formed by trimethylamine and ions formed by all biogenic amines present in the sample, and diagnosing the absence of bacterial vaginosis if the ratio is below a predetermined threshold. The predetermined threshold may be, for example, 0.2.

In one embodiment of the invention, the method comprises diagnosing the absence of bacterial vaginosis if the TMA signal is below a predetermined threshold, which may be, for example, 0.2.

EXAMPLES

Methods

Vaginal swabs were obtained from organs of slaughtered cows, and from live sows in a breeding unit, using a cotton tipped swab by a certified experienced veterinary surgeon and an ion mobility spectrum was obtained of vapors emitted by each sample using an ion mobility spectrometer device after addition of an alkaline solution to the sample on the cotton swab.

In one set of tests, vaginal swabs were collected from 21 sows at the Life Research Institute of Kibbutz Lahav, Israel, and analyzed on Mar. 4, 2009 for bacterial vaginosis (BV). Each sample was placed in a 25 mL polystyrene vial and five drops of KOH were added. The spectra were obtained using a reagent (2-Nonanone) and calibration was carried out with 10 µL of trimethylamine (TMA) that were added to a 25 mL polystyrene vial for calibration as shown in FIG. 1. Permeation tube with 2-nonanone was connected to the drift air during all the trials.

Samples were also collected from the throat of hens with the aid of a swab.

Results

Cows

Figure 2:
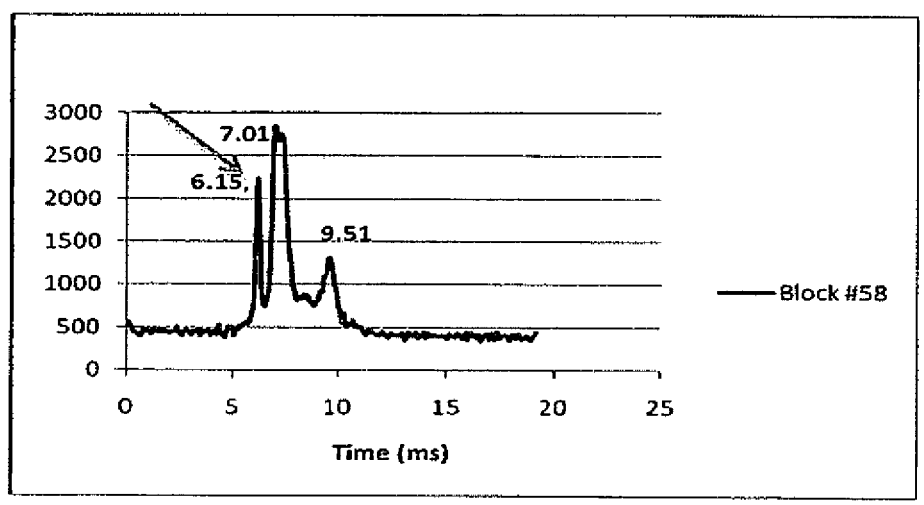
FIG. 2 shows the ion mobility spectrum obtained from a sample of a cow having a high TMA level (peaks at 6.15 ms and 7.01 ms) indicative of vaginal infection.
Figure 3:
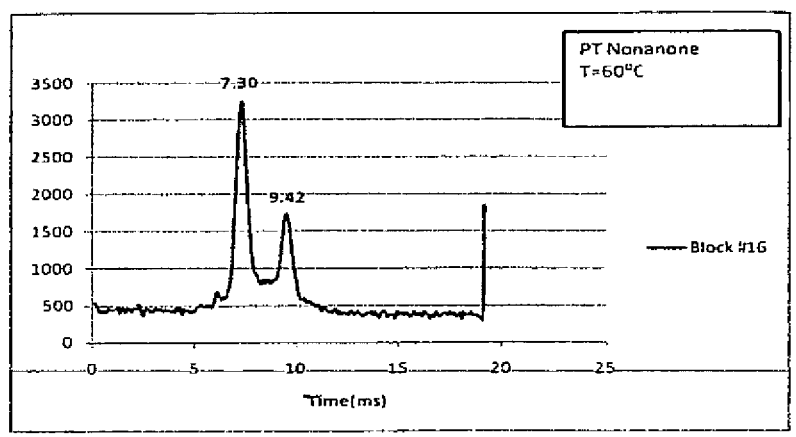
FIG. 3 shows the ion mobility spectrum obtained from a sample from the genitalia of an uninfected cow.

Over 60 samples were collected from three groups of cows. All of the samples collected from the organs of cows (genitalia, lymph nodes, udder, and liver) were obtained in the abattoir and were inspected on site by an experienced veterinarian. One group consisted of 21 genitalia of which five (23.8%) had elevated levels of trimethylamine, indicating that they had a pathological condition in the form of a vaginal infection. A representative spectrum from genitalia having elevated levels of TMA is shown in FIG. 2. FIG. 3 shows a representative spectrum from genitalia having a normal spectrum and is thus negative for bacterial vaginitis ("BV"). Thirteen samples of vaginal discharge fluid were collected from the second group of genitalia and one (7.7%) had an elevated TMA level, while the rest were negative. The third group consisted of 24 cow organs all of which were without elevated TMA levels.

Figure 4:
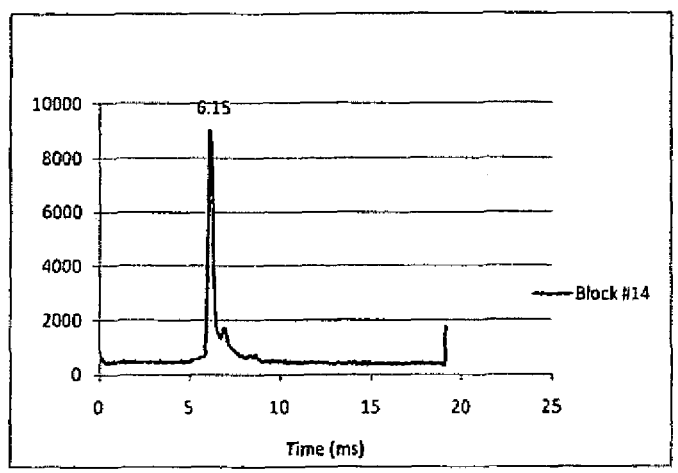
FIG. 4 shows the ion mobility spectrum of a vaginal fluid swab with an extremely large amount of TMA indicating a severe infection.

An even more extreme spectrum is shown in FIG. 4, where the TMA concentration was so high, indicative of a severe infection, that all other ions in the sample transferred their charge to the TMA.

Figure 5:
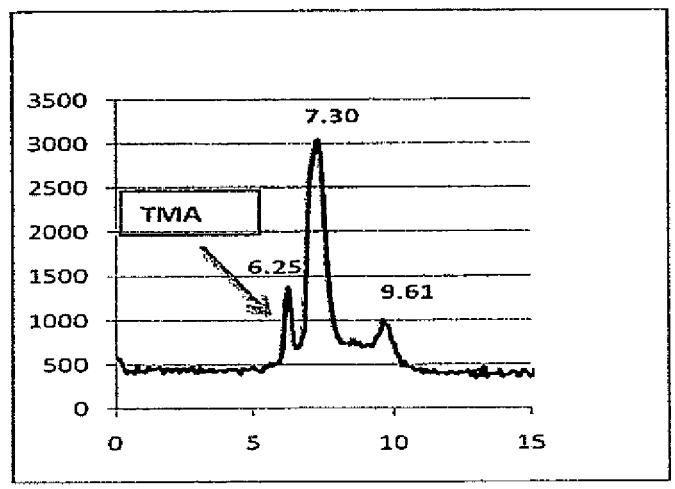
FIG. 5 shows the ion mobility spectrum from a vaginal discharge fluid of a sow indicative of a vaginal infection.
Figure 6:
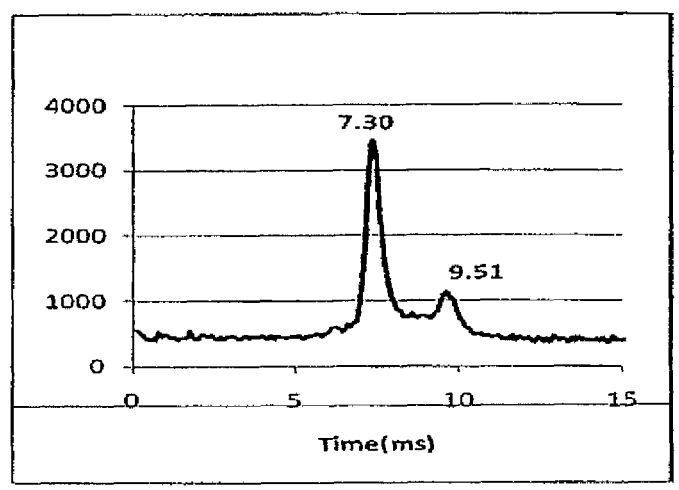
FIG. 6 shows the ion mobility spectrum from a vaginal discharge fluid of an uninfected sow.

In a similar fashion to that disclosed above, vaginal discharge fluid samples were collected from 21 sows in the breeding unit and analyzed. Two samples (9.5%) were found to have elevated levels of TMA indicating vaginal infections, as shown in the representative spectra of FIGS. 5 (positive for BV) and 6 (negative for BV).

Twenty one organ samples were collected from cows on Mar. 8, 2009. The methodology described above for the sows (2-nonanone as a reagent, calibration with TMA) was used in this test as well. The results are summarized in Table 2.

TABLE 2

Summary of diagnostic results for 21 cows.

| Sample No. | IMS Results |
|---|---|
| 1 | negative |
| 2 | negative |
| 3 | Positive(preg.) |
| 4 | negative |
| 5 | negative |
| 6 | negative |

TABLE 2-continued

Summary of diagnostic results for 21 cows.

| Sample No. | IMS Results |
|---|---|
| 7 | negative |
| 8 | positive |
| 9 | negative |
| 10 | positive |
| 11 | positive |
| 12 | positive |
| 13 | negative |
| 14 | negative |
| 15 | negative |
| 16 | negative |
| 17 | negative |
| 18 | negative |
| 19 | negative |
| 20 | negative |
| 21 | negative |

Clinical observations in situ by an experienced veterinarian

| Sample No. | Observations |
|---|---|
| 5 | blood |
| 9 | pus |
| 12 | pus |
| 20 | gave birth recently, mucus with blood |

Figure 7:
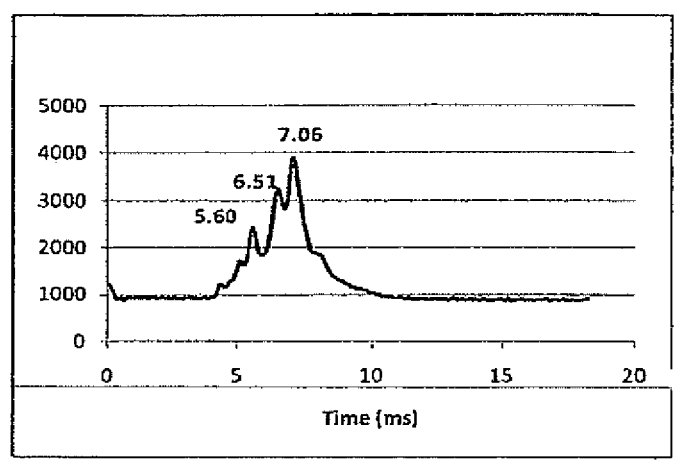
FIG. 7 shows the mobility spectrum obtained from the udder of a cow having an udder inflammation.

A swab sample collected from the udder of a cow with visible udder inflammation was tested. The mobility spectrum of the udder inflammation is shown in FIG. 7. Elevated levels of TMA were clearly seen in the mobility spectrum, while samples collected from a cow without such an inflammation did not have TMA.

A sample collected from lymph nodes of an inflamed organ of a cow also had elevated levels of biogenic amines.

Sows

Figure 8:
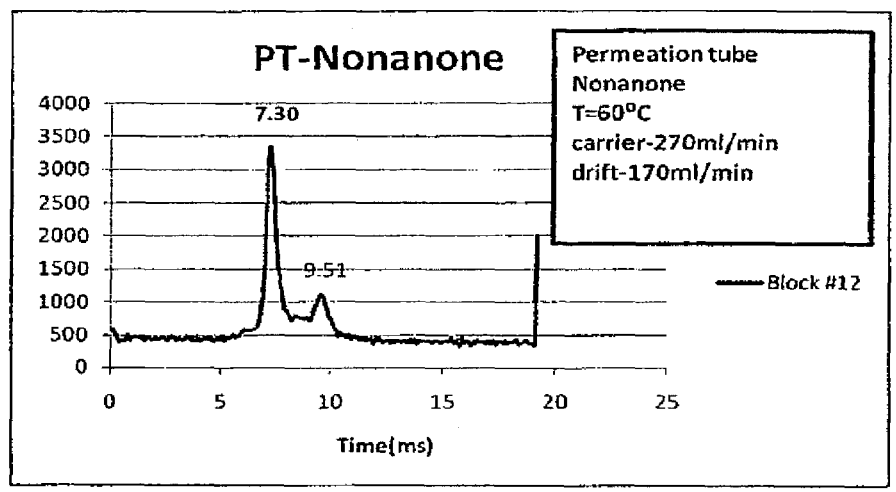
FIG. 8 shows the mobility spectrum obtained with a permeation tube with 2-Nonanone.

A representative ion mobility spectrum of a sample from a sow is displayed in FIG. 8. The results are summarized in Table 1. Two of the 21 samples were clearly contained TMA indicating the presence of a BV infection, and this was confirmed by the veterinarian. Three of the samples were with blood, one had pus and one was extremely malodorous, but this did not affect the diagnosis by IMS.

TABLE 1

Summary of diagnostic results for 21 sows.

| Sample No. | Sow No. | Observations | No. of times giving birth | IMS Result |
|---|---|---|---|---|
| 1 | 1160 | Blood | 3 | negative |
| 2 | 1762 | | 1 | negative |
| 3 | 1550 | | 2 | negative |
| 4 | 9896 | | 4 | negative |
| 5 | 1557 | | 2 | negative |
| 6 | 1238 | | 2 | negative |
| 7 | 1095 | Contaminated with feces* | 3 | negative |
| 8 | 1527 | | 2 | negative |
| 9 | 1812 | | 1 | negative |
| 10 | 8960 | | 7 | negative |
| 11 | 1344 | Blood | 2 | negative |
| 12 | 1756 | | 1 | negative |
| 13 | 1686 | | 1 | negative |
| 14 | 9539 | blood | 5 | positive |
| 15 | 9174 | | 5 | negative |
| 16 | 9544 | | 5 | negative |
| 17 | 1526 | | 2 | negative |

TABLE 1-continued

Summary of diagnostic results for 21 sows.

| Sample No. | Sow No. | Observations | No. of times giving birth | IMS Result |
|---|---|---|---|---|
| 18 | 1515 | | 2 | negative |
| 19 | 9552 | Turbid and malodorous* | 5 | positive |
| 20 | 9817 | | 4 | negative |
| 21 | 8417 | pus | 9 | negative |

*Contamination did not interfere with the test.

Figure 9:
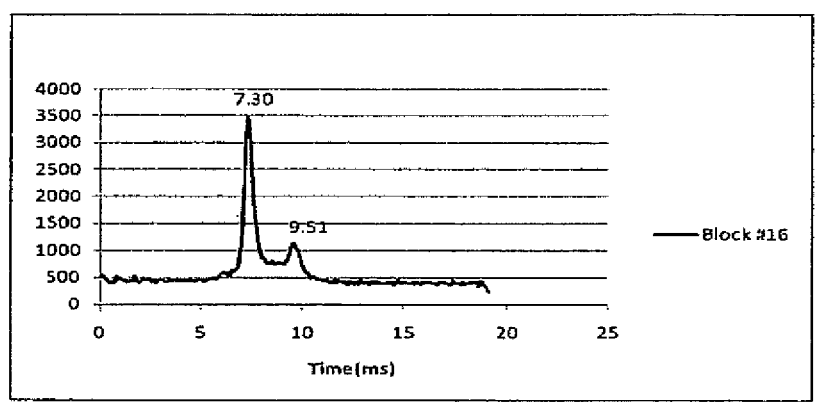
FIG. 9 shows the mobility spectrum obtained from a sow not having a vaginal infection.
Figure 10:
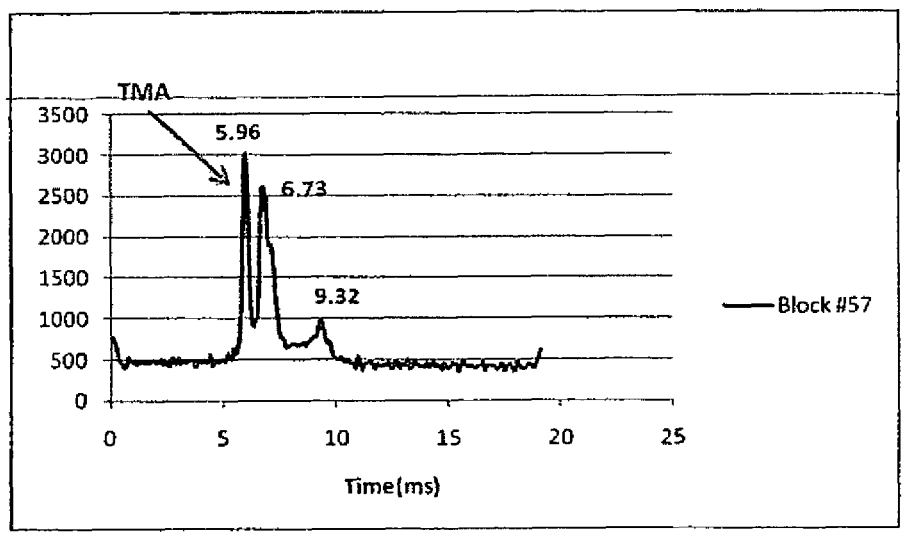
FIG. 10 shows the mobility spectrum obtained from a sow having BV.
Figure 11:
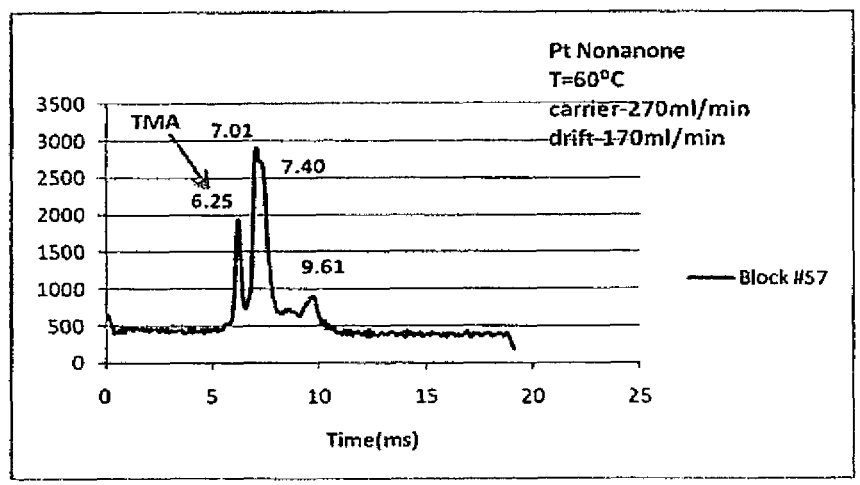
FIG. 11 shows the mobility spectrum obtained from a sow with BV.

All of the uninfected samples tested produced the same spectrum, a representative spectrum of which is shown in FIG. 9. The positive samples were tested twice, in order to confirm the results. A representative spectrum obtained from the second measurement of a vaginal sample of a sow infected with BV in shown in FIG. 10. Another example from an infected sow is shown in FIG. 11.

Diagnosis of Bronchitis in Chicken

Swab samples were collected from the throats of 10 chickens and were tested by IMS. One of the samples contained elevated levels of TMA and the chicken was diagnosed by the veterinarian as having a bronchitis infection.

Example 1

In this example, the Ion Mobility Spectrometers (IMS) used were PhemtoChem-100 made by PCP Inc., West Palm Beach, Fla., USA and PTIMS made by Rotem Industries, Mishor Yamin, Israel. However, any properly equipped IMS made be used to obtain such spectra. The first and second elaborators, in this example, are combined into a single computer which comprises a permanent memory, a buffer memory, a CPU, a screen, a BUS providing the necessary electrical connections, power means, a keyboard, and all obvious accessories. Generally, IMS may display the biogenic amine spectrum or display their results in the form of a histogram series of bars or as a table of compounds. In any case, the IMS transmits to the buffer memory the amine spectrum. The operator has chosen, by means of the keyboard, the type of response which he wants. In this case, he has chosen a response which relates to the presence of a cancer. The CPU is programmed to draw from the buffer memory the data of the amine spectrum and calculate from them the measured parameters which are relevant to the diagnosis of cancer, according to a program which is stored in the permanent memory and which the CPU has drawn from said memory once the operator's choice has been made. The CPU also draws from the permanent memory the comparative parameters and carries out the necessary comparison to draw the response required.

Figure 12:
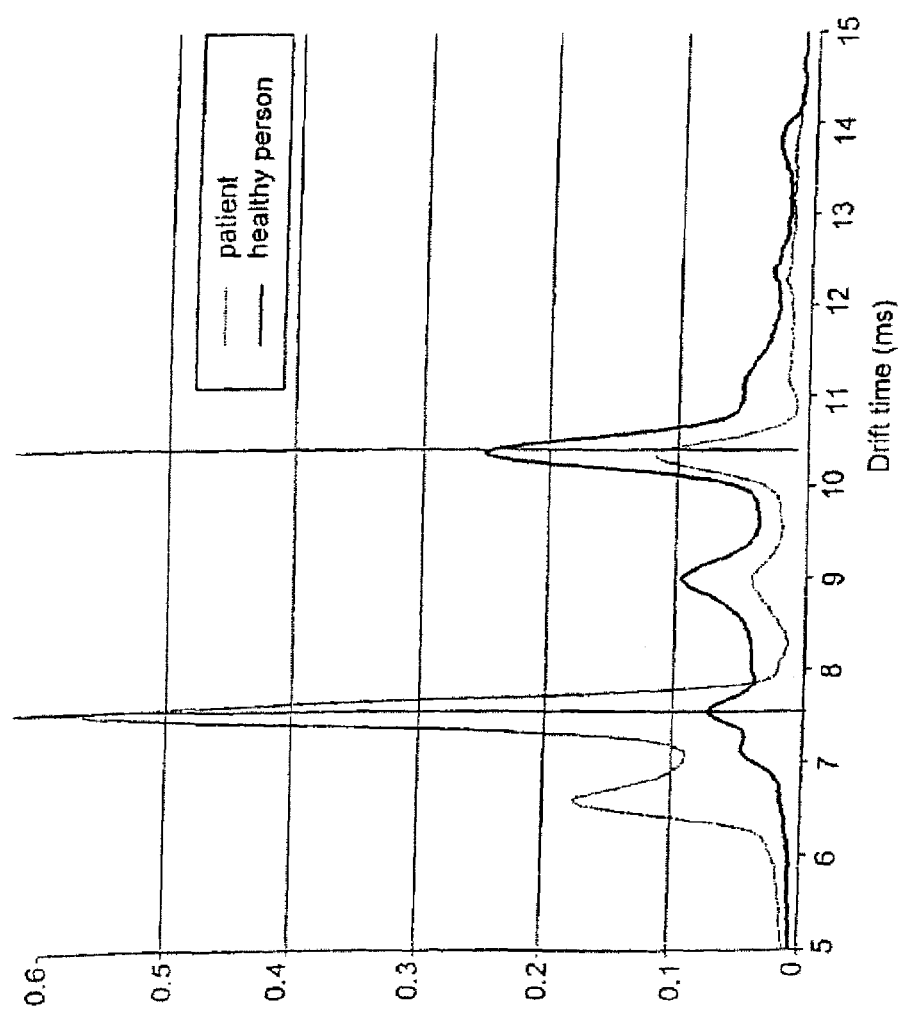
FIG. 12 is a graphical representation of the biogenic amine spectrum of the urine of a cancer patient and the comparable spectrum of a healthy subject.

FIG. 12 shows two curves relating to a healthy person and to a cancer patient respectively, as indicated in the drawing. The abscissa is the time at which the various amines appear and the ordinate is their amount, and since the various amines appear at different time, each curve constitutes an amine spectrum. The different peaks that appear permit to diagnose the presence of a disease, in this case cancer.

Example 2

Figure 13:
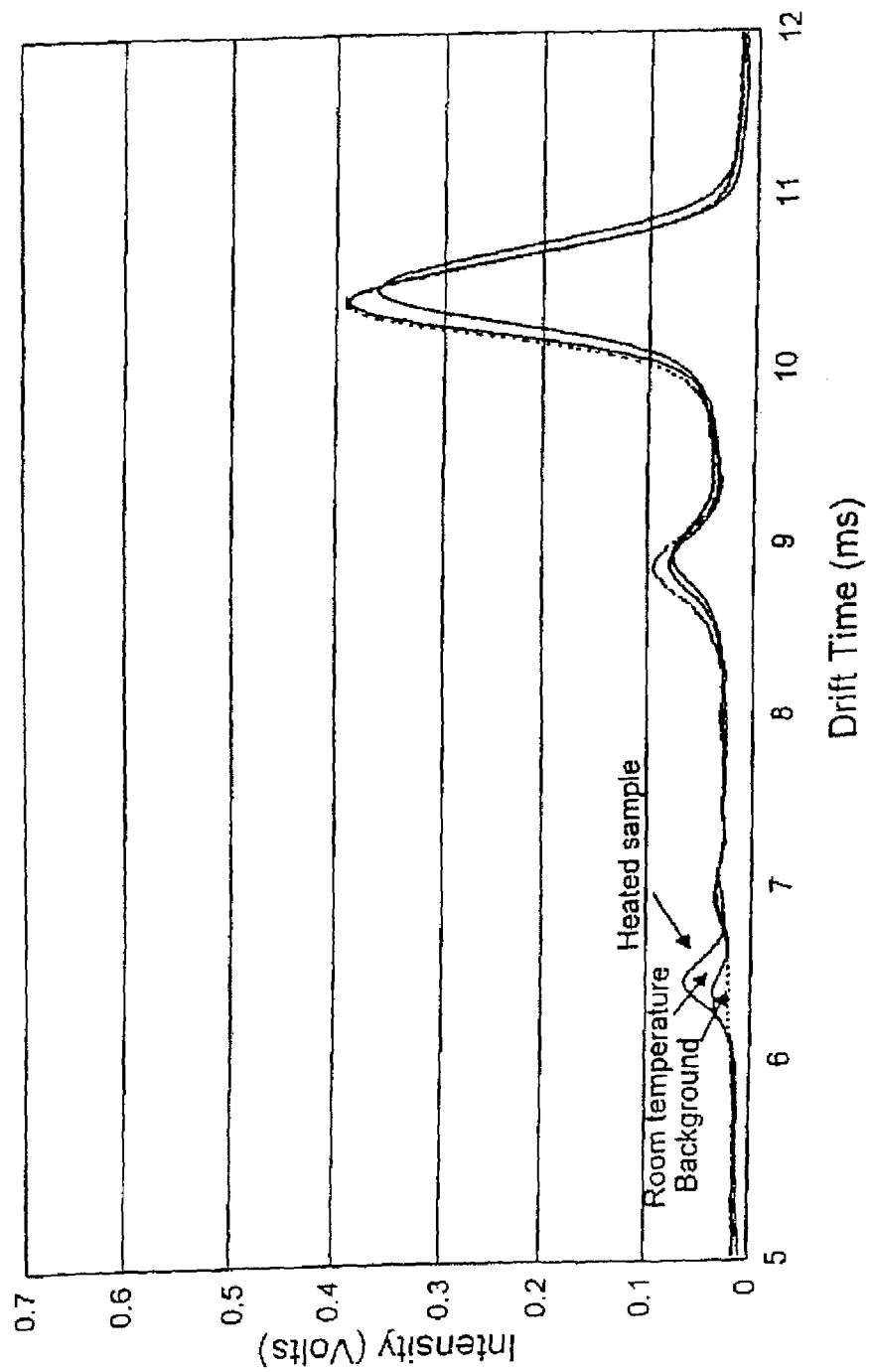
FIG. 13 is a graphical representation showing the mobility spectra of a sample of 0.1 mL of a mixture containing putrescine, cadaverine, TMA (25:50:5 mmoles), obtained without the addition of a reagent; two solid lines indicating the spectra obtained at room temperature and under heating, while a broken line indicates the background mobility spectrum of the instrument used.
Figure 14:
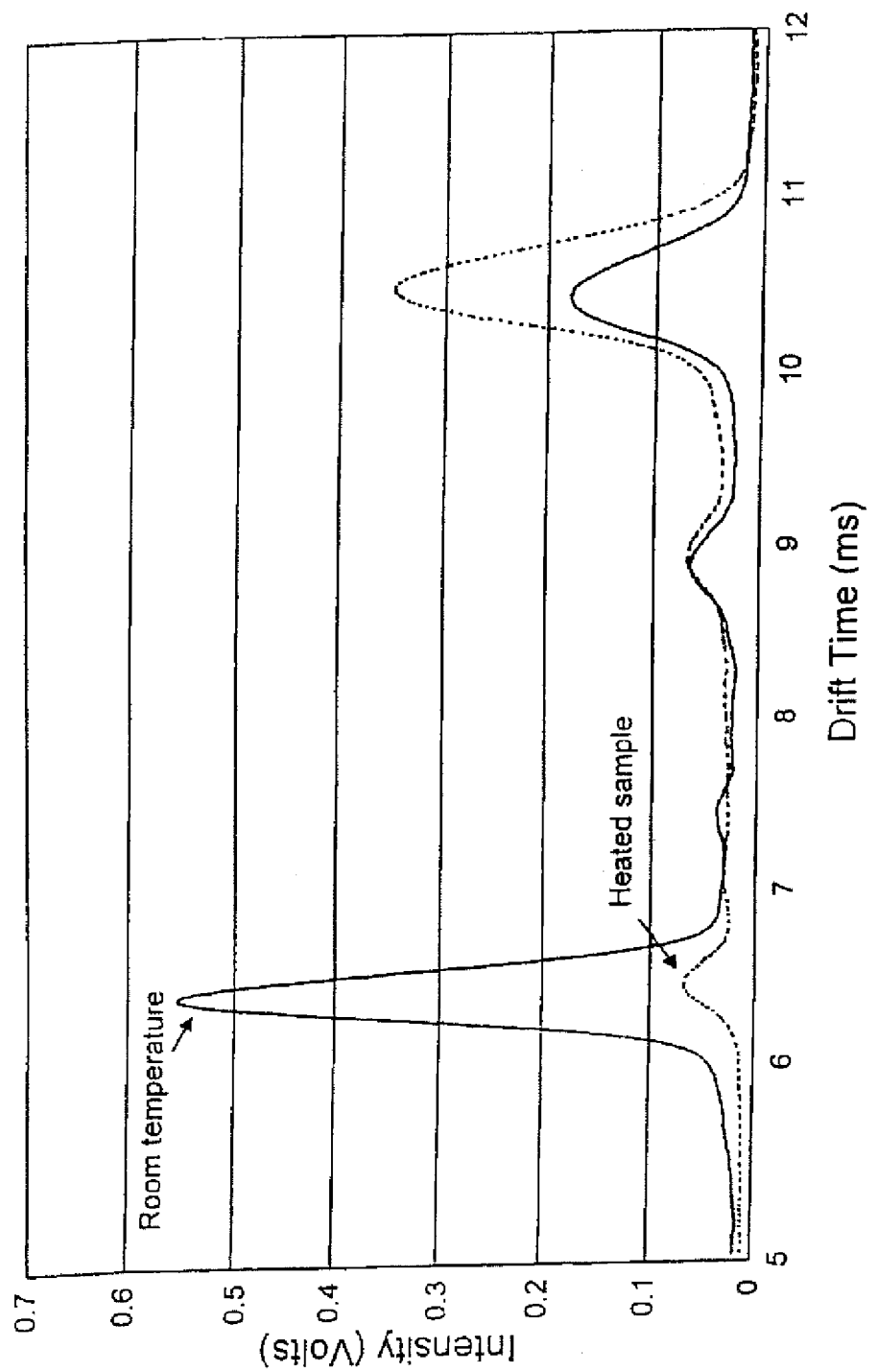
FIGS. 14 to 21 are graphical representations of each of two mobility spectra: one obtained at room temperature, shown in solid lines, and one obtained during heating which raised the temperature of the sample to about 60° C., shown on broken lines; the abscissas indicating the time in milliseconds (msec) and the ordinates indicating the signal intensity in volts, which is proportional to the amount of each amine emanated, under the conditions of the various experiments.
Figure 15:
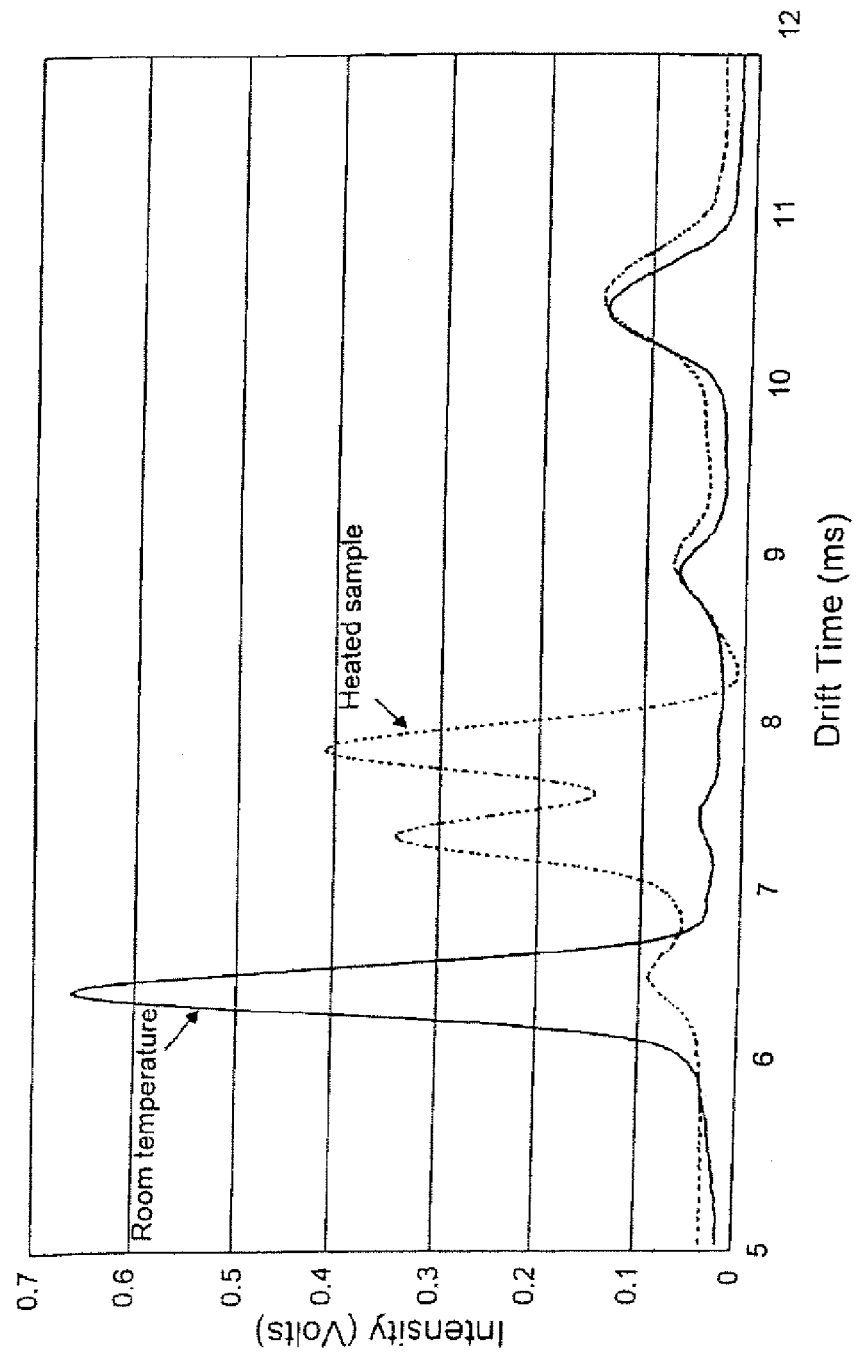

A sample of 0.1 mL of a mixture ("cocktail") containing 25:50:5 mmoles putrescine:cadaverine:TMA (220:510:29.5 ng (nanograms) in sample) was analyzed by IMS.

a) FIG. 13—Without reagents at room temperature (23° C.) and during immersion in hot water (94° C.). As clearly indicated in the drawing, one curve was obtained at room temperature and another curve was obtained when the sample was immersed in hot water. Further, the broken line shows the background mobility spectrum of the instrument. The biogenic amines were not identified.

b) FIG. 14—After addition of 0.3 mL of 4N KOH solution at room temperature (23° C.) and during immersion in hot water (94° C.). The curve in solid line was obtained at room temperature; the curve in dashed line was obtained when the sample was immersed in hot water. A large TMA peak was observed at room temperature, but once the sample was heated, most of the TMA was boiled off. The other biogenic amines were not identified.

c) FIG. 15—After addition of 1 drop 10% $HNO_3$ followed by the addition of 0.3 mL of 4N KOH solution at room temperature (23° C.) and during immersion in hot water (94° C.). The curve in solid line was obtained at room temperature; the curve in dashed line was obtained when the sample was immersed in hot water. The TMA peak is similar in intensity to that in FIG. 14, but heating results in large peaks for cadaverine and putrescine, which could not be observed previously.

Example 3

Figure 16:
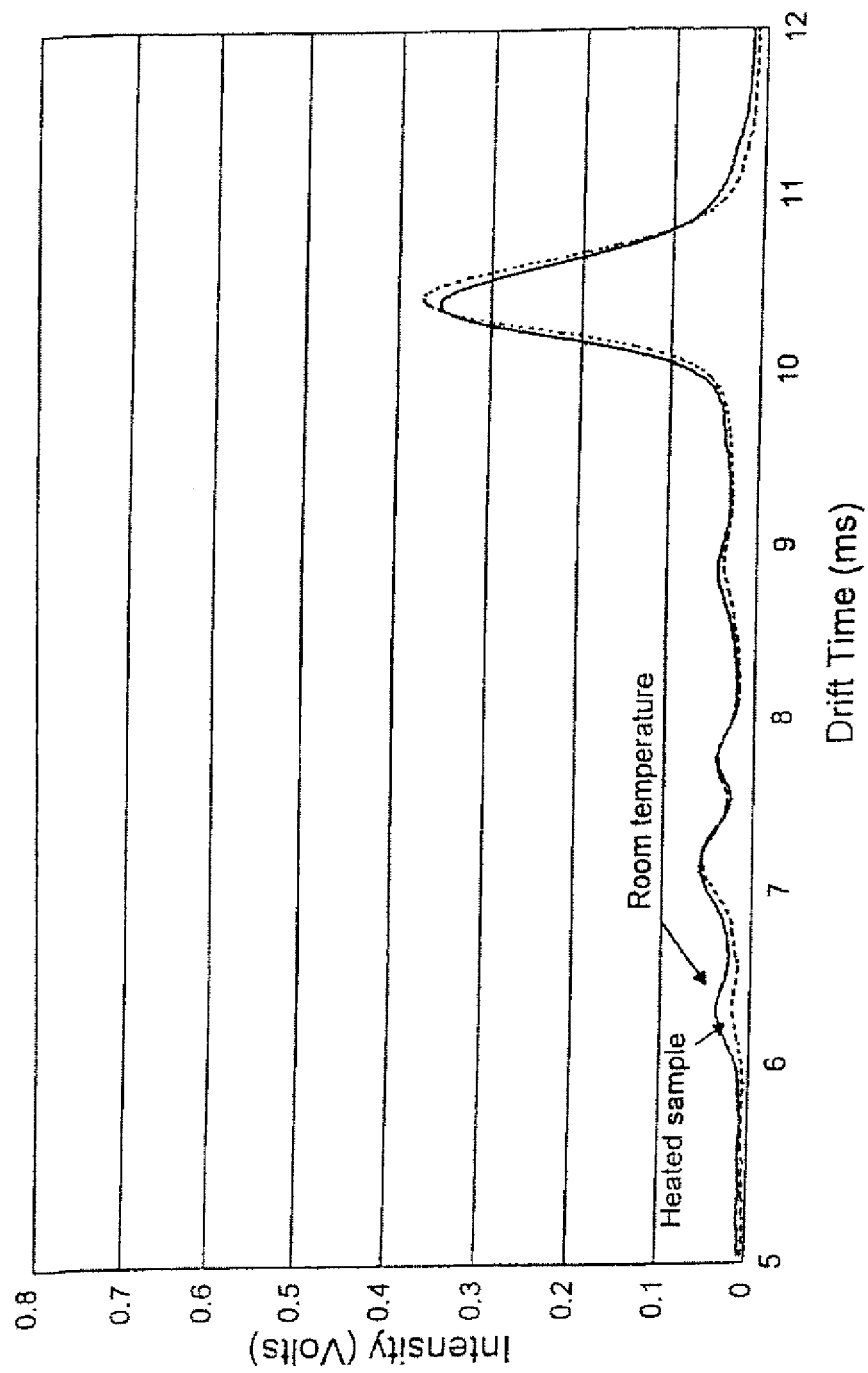
Figure 17:
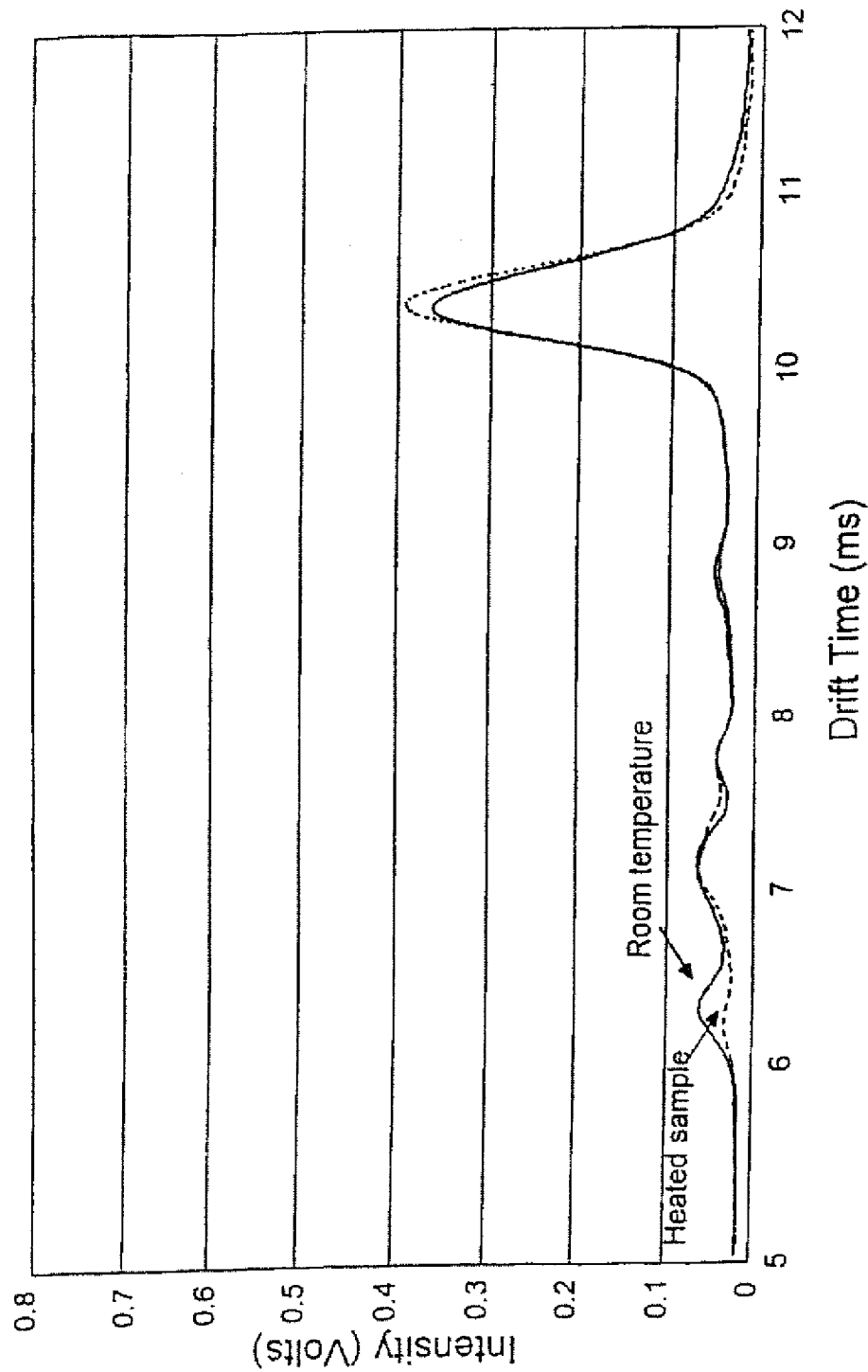
Figure 18:
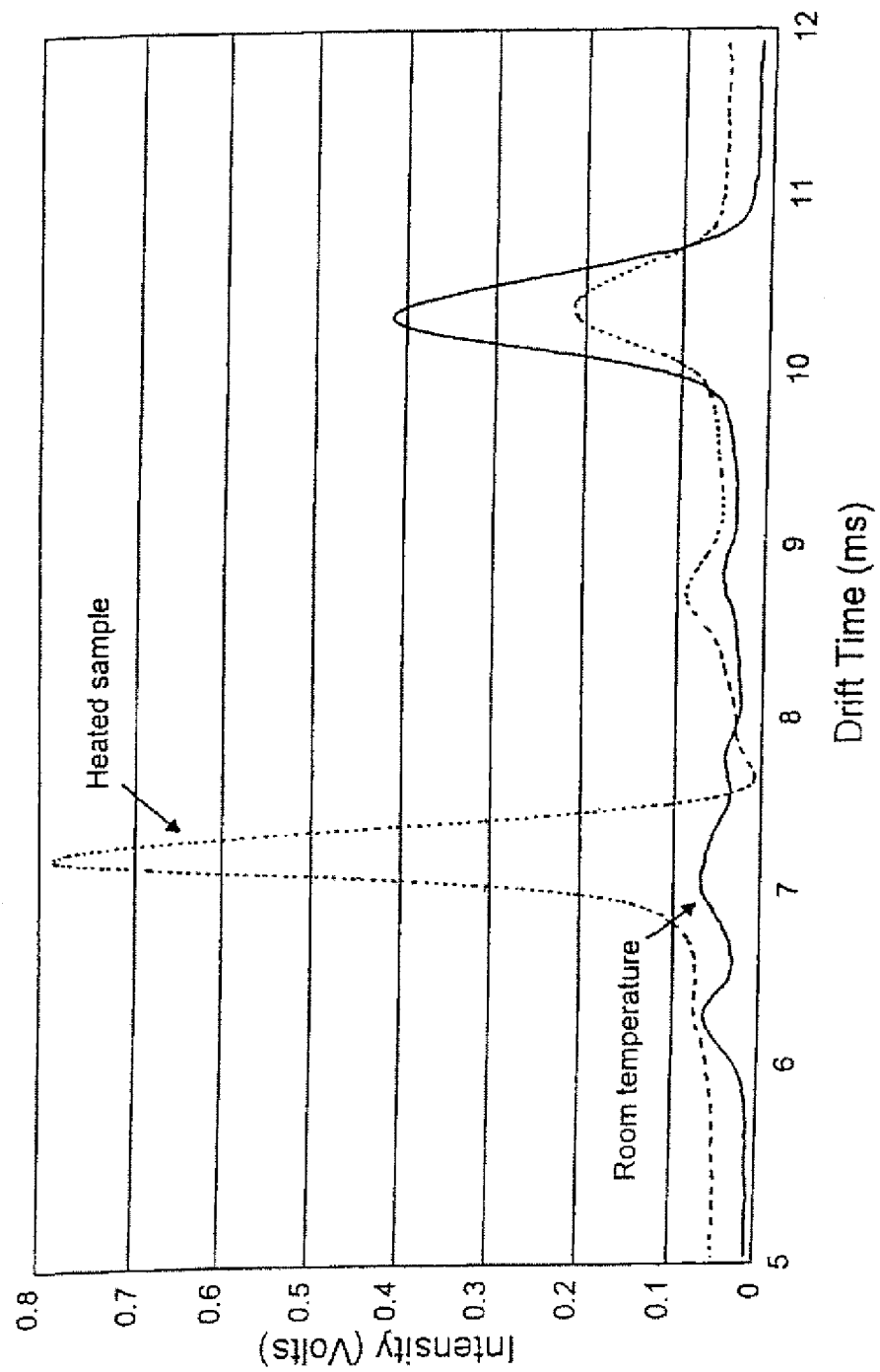

A 0.1 mL sample, collected by rinsing the vagina with 2 mL of saline solution from a female patient with a vaginal infection, was analyzed by IMS:

a) FIG. 16—Without reagents at room temperature (23° C.) and during immersion in hot water (94° C.). The curve in solid line was obtained at room temperature; the curve in dashed line was obtained when the sample was immersed in hot water. Biogenic amines were not identified.

b) FIG. 17—After addition of 0.3 mL of 4N KOH solution at room temperature (23° C.) and during immersion in hot water (94° C.). The curve in solid line was obtained at room temperature; the curve in dashed line was obtained when the sample was immersed in hot water. Biogenic amines were not identified.

c) FIG. 18—After addition of 1 drop 10% $HNO_3$ followed by the addition of 0.3 mL of 4N KOH solution at room temperature (23° C.) and during immersion in hot water (94° C.). The curve in solid line was obtained at room temperature; the curve in dashed line was obtained when the sample was immersed in hot water. The presence of putrescine was clearly observed in the mobility spectrum of the heated sample.

Example 4

Figure 19:
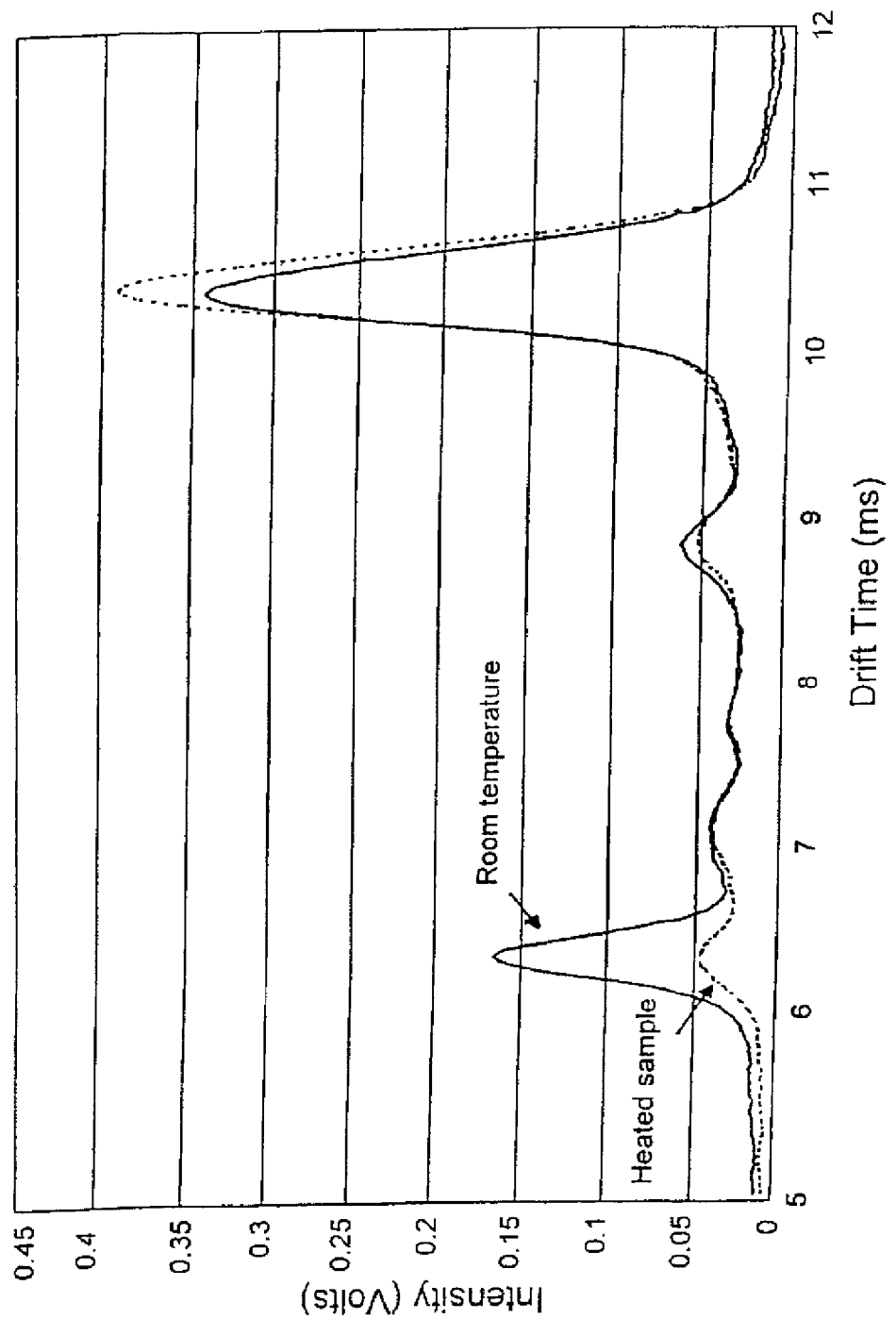
Figure 20:
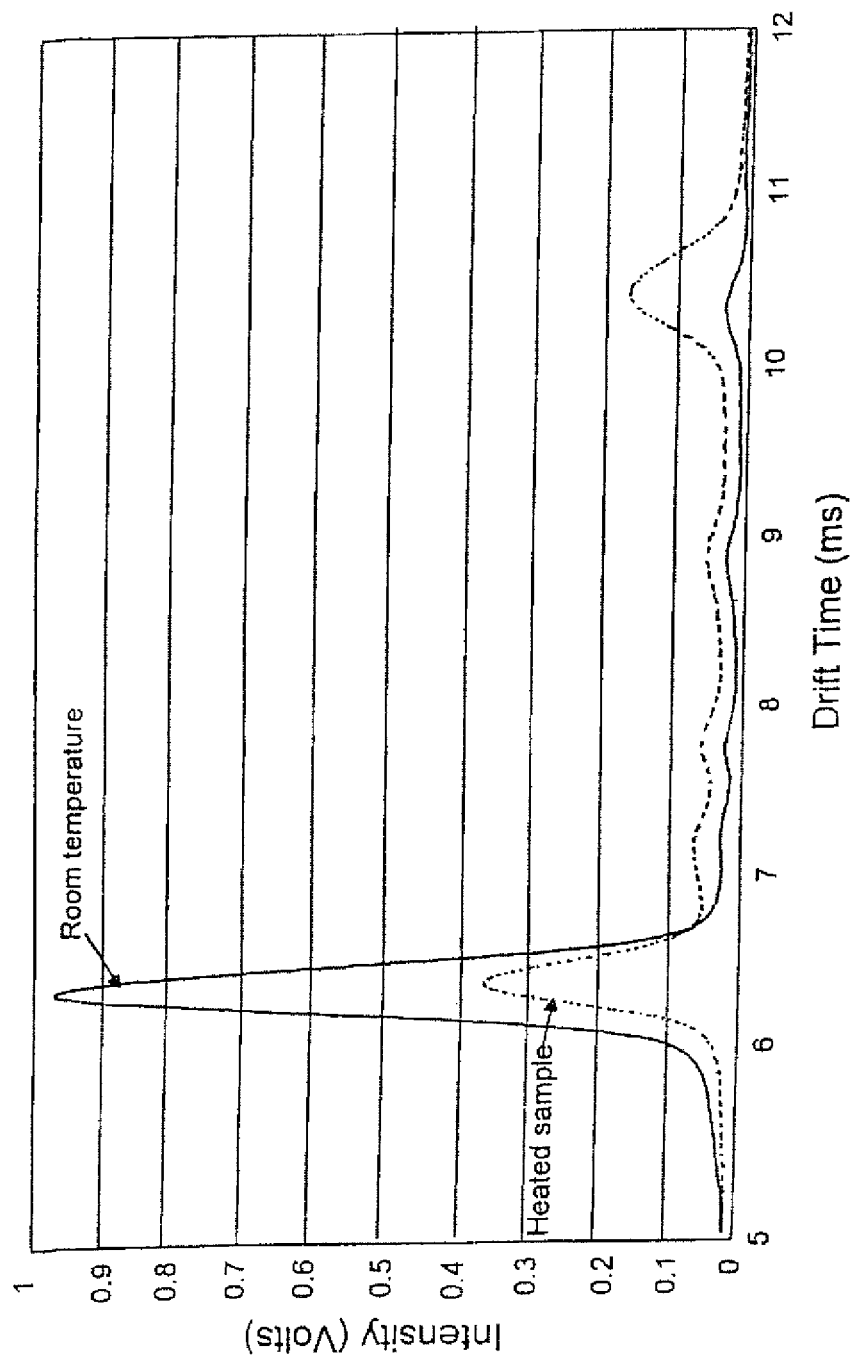
Figure 21:
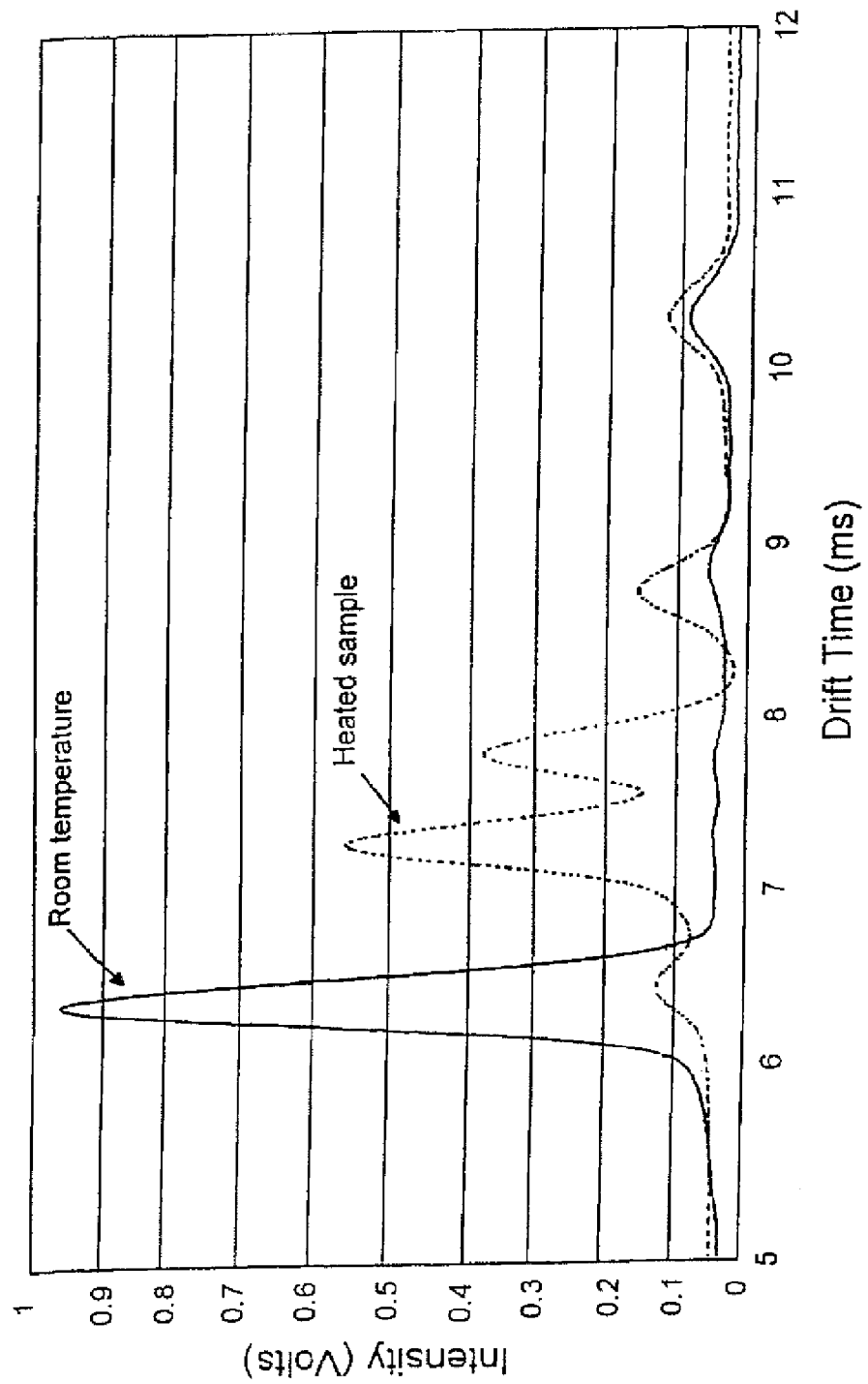

A sample collected from a piece of chicken after one day in a refrigerator, was analyzed by IMS:

a) FIG. 19—Without reagents at room temperature (23° C.) and during immersion in hot water (94° C.). The curve in solid line was obtained at room temperature; the curve in dashed line was obtained when the sample was immersed in hot water. A small TMA peak was observed, but other biogenic amines were not identified.

b) FIG. 20—After addition of 0.3 mL of 4N KOH solution at room temperature (23° C.) and during immersion in hot water (94° C.). The curve in solid line was obtained at room temperature; the curve in dashed line was obtained when the sample was immersed in hot water. The TMA peak was larger at RT, but other biogenic amines were not identified.

c) FIG. 21—After addition of 1 drop 10% $HNO_3$ followed by the addition of 0.3 mL of 4N KOH solution at room temperature (23° C.) and during immersion in hot water (94° C.). The curve in solid line was obtained at room temperature; the curve in dashed line was obtained when the sample was immersed in hot water. The presence of putrescine and cadaverine were clearly observed in the mobility spectrum of the heated sample, while the TMA peak was large at RT.

The same instrument is used for all the measurements and therefore the background spectrum shown in FIG. 13 is not repeated in the following figures. The instrument used was a prototype ion mobility spectrometer (PT-IMS) made by Rotem Industries Ltd., Israel.

In the drawings, the abscissa indicates time in milliseconds and the ordinate indicates the amount of each amine emanated, under the conditions of the various experiments, as units of volts. In FIG. 13, a broken line indicates the background mobility spectrum of the instrument used. The same instrument is used for all the measurements and therefore said background spectrum is not repeated in the following figures. The instrument used was the aforesaid PT-IMS.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for diagnosing a disease or pathological condition in a non-human animal comprising:
   a. obtaining a body sample from the animal;
   b. successively adding, in any order, a strong acid and a strong base to the sample to effect a basic pH;
   c. carrying out an ion mobility spectrometry or a differential mobility spectrometry measurement on the sample thereby determining an amount of ions formed by at least two biogenic amines contained in the sample; and
   d. calculating a ratio of the amounts of ions formed by the different biogenic amines in the sample, wherein the ratio is indicative of the disease or pathological condition.

2. The method of claim 1, wherein the body sample is taken from the group consisting of male genitalia, female genitalia, udder, liver, heart, muscle, brain, tongue, throat, lungs, skin, and lymph node.

3. The method of claim 1, wherein the disease or pathological condition is selected from the group consisting of bacterial vaginosis, inflammation, and bronchitis.

4. The method of claim 1, wherein the disease or pathological condition is caused by bacteria, viruses, anaerobic microorganisms, or fungi.

5. The method of claim 1, wherein the amines are selected from the group consisting of putrescine and cadaverine.

6. The method of claim 1, wherein the body sample is a sample of vaginal fluid, wherein at least one of the amines present in the sample is trimethylamine, and wherein the pathological conditions comprise vaginal disorders.

7. The method of claim 6, further comprising calculating a ratio of the amounts of ions formed by trimethylamine and ions formed by all biogenic amines present in the sample, and diagnosing the presence of bacterial vaginosis if the ratio is above a predetermined threshold.

8. The method according to claim 7, wherein the predetermined threshold is 0.4.

9. The method of claim 6, comprising diagnosing a presence of bacterial vaginosis if a ratio trimethylamine signal is above a predetermined threshold.

10. The method of claim 6, comprising calculating a ratio of the amounts of ions formed by trimethylamine and ions formed by all biogenic amines present in the sample, and diagnosing an absence of bacterial vaginosis if the ratio is below a predetermined threshold.

11. The method of claim 10, wherein the predetermined threshold is 0.2.

12. The method of claim 1, comprising calculating a ratio of the amounts of ions formed by trimethylamine and ions formed by all biogenic amines present in the sample, and diagnosing an absence of bacterial vaginosis if a trimethylamine signal is below a predetermined threshold.

13. The method of claim 1, wherein abnormally high amounts of putrescine or cadaverine indicate a pathological condition.

14. The method of claim 1, wherein the disease or pathological condition is cancer.

* * * * *